United States Patent [19]
Feder et al.

[11] 4,087,327
[45] May 2, 1978

[54] MAMMALION CELL CULTURE PROCESS

[75] Inventors: Joseph Feder; Katharine Ku, both of University City; Mau-Jung Kuo, Creve Coeur, all of Mo.

[73] Assignee: Monsanto Company, St. Louis, Mo.

[21] Appl. No.: 676,100

[22] Filed: Apr. 12, 1976

[51] Int. Cl.$^2$ ............................ C12K 9/00; C12B 1/10
[52] U.S. Cl. ...................................... 195/1.7; 195/127
[58] Field of Search ................ 195/127, 139, 1.8, 1.7, 195/142, 144; 210/321, 500

[56] References Cited

U.S. PATENT DOCUMENTS

| | | | |
|---|---|---|---|
| 3,342,729 | 9/1967 | Strand | 195/127 |
| 3,746,175 | 7/1973 | Markley | 210/321 |
| 3,821,087 | 6/1974 | Knazek et al. | 195/127 |
| 3,843,454 | 10/1974 | Weiss | 195/127 |
| 3,883,393 | 5/1975 | Knazek et al. | 195/1.8 |
| 3,997,396 | 12/1976 | Delente | 195/1.8 |

OTHER PUBLICATIONS

Schratter, "Synthetic Capillaries for Cell Culture," American Laboratory, vol. 6, No. 10 (Oct. 1974), pp. 33–38.
Bulletin of Amicon Corporation, 1975, "Membrane Perfusion by Artificial Capillaries."
Williams et al, "A Hollow Filament Fabric Blood Oxygenator", Proceedings Artificial Heart Program Conference, NIH, Bethesda, (1969), pp. 365–371.

*Primary Examiner*—Alvin E. Tanenholtz
*Assistant Examiner*—Thomas G. Wiseman
*Attorney, Agent, or Firm*—Scott J. Meyer; John D. Upham

[57] ABSTRACT

A cell culture reactor system is provided for the growth of cells in vitro which employs elongate hollow or solid fibers arranged in a shallow layer configuration as a matrix for cell attachment in which the flow path of the culture media is directed substantially uniformly through the fiber layer and substantially transverse to the plane of the elongate axes of the fibers.

6 Claims, 5 Drawing Figures

MAMMALION CELL CULTURE PROCESS

BACKGROUND OF THE INVENTION

This invention relates to a method and apparatus for the culturing of cells.

The culturing of living cells in vitro is desired for a variety of purposes such as the preparation of viral vaccines, the recovery of valuable by-products of the cell metabolism and the production of tissue-like densities for creating artificial organs.

Various procedures have been developed previously for the culturing of cells in vitro. One widely used method involves attaching and growing the cells on the interior surface of glass or plastic roller tubes and bottles. This method is exemplified by use of the Flow tube (Flow Laboratories) disclosed in U.S. Pat. No. 3,450,598. Another procedure used heretofore attaches and grows the cells on the flat side of appropriately shaped stationary containers such as, for example, the ordinary petri dish or rectangular shaped culture plates. The flat surface method also has been employed in apparatus having a stack of plates comprising a continuous plastic sheet arranged around a set of spaced-apart supports as illustrated in U.S. Pat. No. 3,843,454. Instead of using bare glass or plastic as the support surface for growing cells as monolayers, collagen-coated glass also has been employed. In order to provide a 3-dimensional support matrix for cell culturing, use of a collagen-coated cellulose sponge has been suggested heretofore.

Further background information on these and other such conventional cell culturing methods can be had by reference to a standard text in the field such as Kruse and Patterson, "Tissue Culture Methods and Applications," Academic Press, New York, 1973.

Recently, the use of hollow fibers or synthetic capillaries has been disclosed as a support matrix for the propagation of cells. This use was reported by Knazek, Science 178, 65–67 (1972), and specific apparatus for this cell culturing method is described in U.S. pat. Nos. 3,821,087 and 3,883,393. The apparatus comprises a bundle of ultrafiltration fibers retained in a cylindrical shell or cartridge. In essence, the apparatus employs membrane perfusion by artificial capillaries. The extensive surface area of the hollow fiber system allows selective transport through the fiber walls and facilitates molecular exchange between the stream flowing through the fiber interiors and a liquid which bathes the outer surfaces of the fibers by a simple gradient diffusion. This hollow fiber apparatus is further described by Knazek in Federation Proc. 33, 1978-81 (1974), and in Exptl. Cell Res. 84, 251-4 (1974) wherein it is used to produce HCG hormone from human choriocarcinoma cells at a rate eleven times higher than that grown on 75 cm.$^2$ monolayer flasks (Falcon). Cartridge apparatus of the type disclosed by Knazek is commercially available from Amicon Corporation and its use in cell culturing is described in American Lab. October 1974, pp. 33–38.

Notwithstanding the usefulness of the Knazek apparatus and method, it has been found in practice that employment of the bundle or cartridge configuration with fluid flow of culture medium through the elongate capillary membranes prevents complete penetration of the fiber bundle by the cells and sets up an undesirable gradient of medium flow. The inability of the cells to fully penetrate the fiber bundle results in uneven dispersion of the cells and incomplete utilization of the available fiber surface for cell attachment. The undesirable gradient consists of an uneven distribution and utilization of liquid culture medium. As the medium flows through the reactor, nutrients are more available to the cells near the inlet, and as the medium flows to the outlet, metabolic products such as lactic acid accumulate in the medium, thereby undesirably affecting pH and producing other toxic effects on the cells.

BRIEF SUMMARY OF THE INVENTION

In accordance with the present invention, a method and apparatus for the growth of cells in vitro is provided which employs elongate hollow or solid fibers in a shallow layer configuration as a matrix for cell attachment in which the flow path of culture media is directed substantially uniformly through the fiber layer and substantially normal or transverse to the plane of the elongate axes of the fibers. A relatively shallow bed of fibers and a relatively short path of media flow are thus employed whereby the gradient of nutrients and metabolic products is substantially reduced from that produced by the bundle or cartridge configuration of the prior art and a more extensive utilization of fiber surface is obtained. By the term shallow layer is meant a layer or bed in which the length and width are substantially greater than the distance therebetween or thickness of the layer.

DETAILED DESCRIPTION OF THE INVENTION

In the present invention, several variations of the cell culture method and apparatus are contemplated by the inventors. While the specification concludes with claims particularly pointing out and distinctly claiming the subject matter regarded as forming the present invention, it is believed that the invention and its advantages will be better understood from the following description of the preferred embodiments taken in connection with the accompanying drawings in which:

Figure 1:
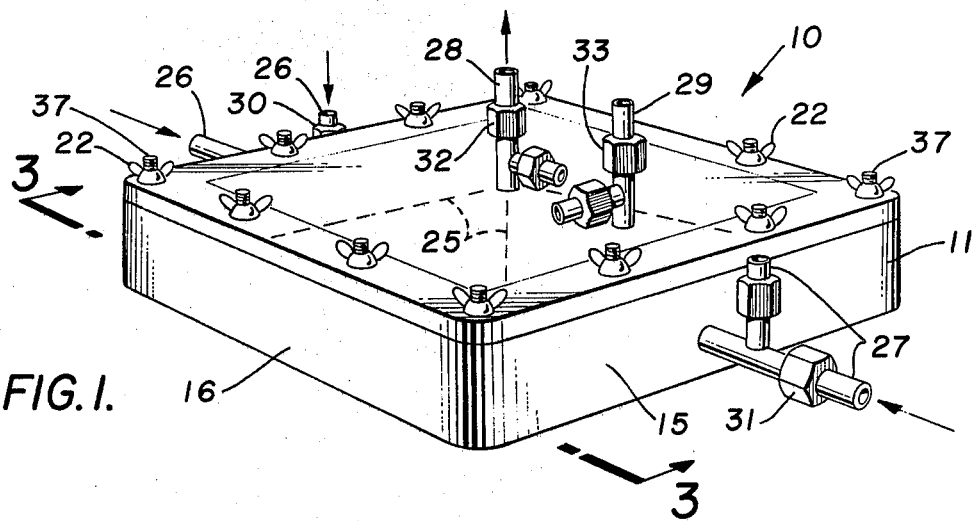
FIG. 1 is a perspective of one embodiment of the cell culture apparatus of the invention.
Figure 2:
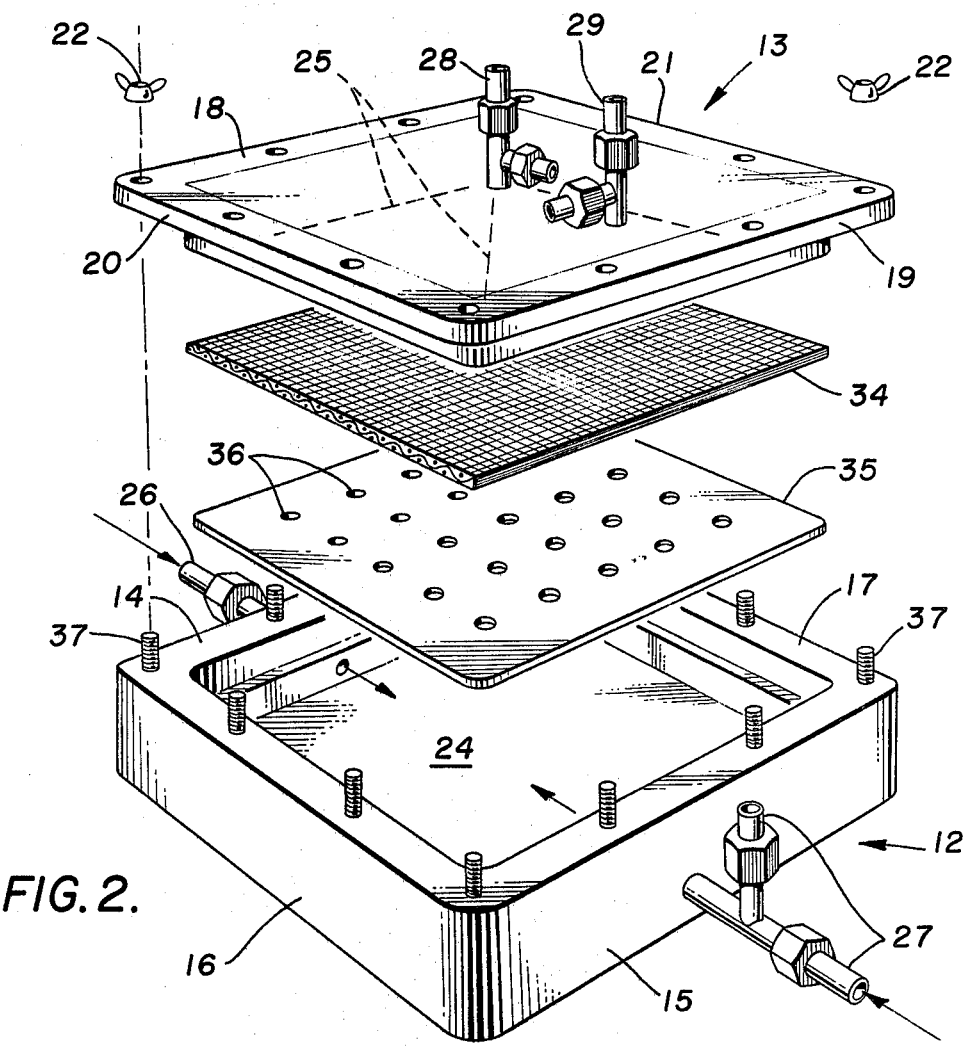
FIG. 2 is an exploded view of the apparatus of FIG. 1 showing the internal parts.
Figure 3:
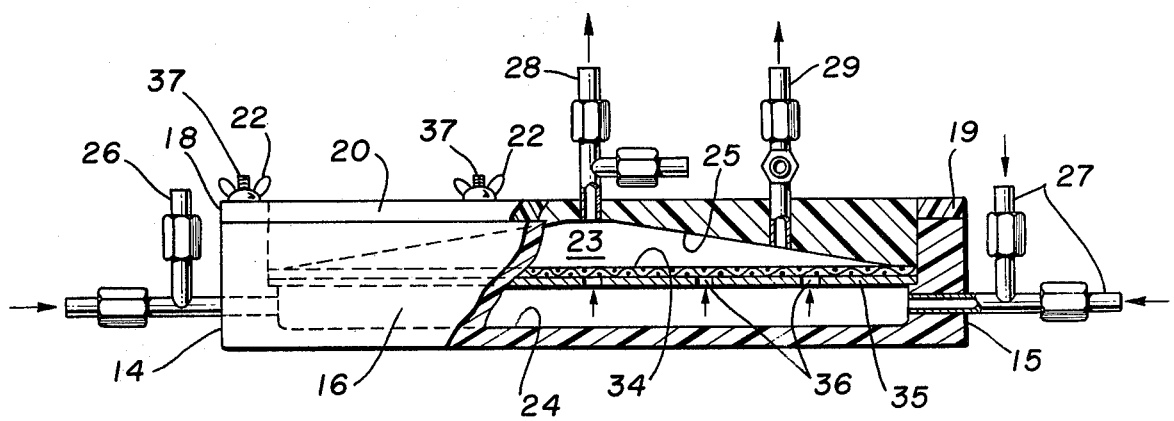
FIG. 3 is an end view taken along the line 3—3 of FIG. 1.

Turning now to FIGS. 1 to 3 of the drawings, reference numeral 10 refers generally to a cell culture reactor. Reactor 10 is comprised of a generally rectangular parallelipiped housing 11 having separable lower part 12 and upper part 13. Lower housing part 12 has parallel sidewalls 14 and 15 and parallel endwalls 16 and 17. Similarly, upper housing part 13 has parallel sidewalls 18 and 19 and parallel endwalls 20 and 21. In upper housing part 13, the lower portions of walls 18, 19, 20 and 21 are recessed to fit snugly within the confines of the inner sides of walls 14, 15, 16 and 17, respectively, of lower housing part 12, while the upper flange portions of walls 18, 19, 20 and 21 are adapted to seat flush on the upper rim of walls 14, 15, 16 and 17.

The two parts of housing 11 are suitably secured together with conventional fastener means such as clamps, screws, or bolts 37 with wing nuts 22 as illustrated, and the like means. An adhesive closure means for the two housing parts also can be employed, if desired.

In the closed position, parts 12 and 13 define a chamber 23 inside the housing. The bottom wall 24 of the housing is essentially flat; whereas, the top wall 25 of the housing, as illustrated, has a generally conical shape whereby chamber 23 decreases in depth in all directions as it radiates from the center of top wall 25.

Disposed in the walls of reactor 10 and communicating with chamber 23 are media inlet ports 26 and 27 in the bottom part of housing 11, and media outlet port 28 in the center of the top part of the housing. The media inlet ports also communicate with a media supply source and pumping or gravity feeding means (not shown) while the media outlet port also communicates with a spent media collection vessel (not shown). An access port 29, which can be used for inoculation and sampling, also is disposed within the top part of housing 11. Each of ports 26, 27, 28 and 29 have adapters 30, 31, 32 and 33, respectively, which can be used for regulation of the media flow and the distribution of media into the cell reactor.

A layer of elongate fibers 34 is arranged in a relatively shallow, flat bed configuration within chamber 23 and supported by a rectangular distributor plate 35. A plurality of small openings 36 are substantially equidistantly spaced apart on the surface of plate 35 for upward passage of media. These openings or perforations can be, for example, from about 1 to about 10 millimeters in diameter and can be conveniently spaced apart, for example, up to about ten centimeters apart. Plate 35 is suitably mounted within chamber 23 such that it lies in a substantially horizontal plane above the media inlets 26 and 27. Such mounting can be provided by conventional support means such as brackets, flanges, adhesive sealing and the like means.

The elongate fibers which are used for cell attachment in the cell culture reactor 10 can be hollow tubes or solid filaments ranging generally from about 100 to about 1000 microns in diameter. These fibers can be produced from any suitable material which is non-toxic to the cells and can be appropriately spun into fibers and which permits cell attachment thereto. Suitable materials include, for example, various acrylonitrile polymers, styrene polymers, polyionic polymers, polycarbonates, polysulfones, polycarbohydrates such as cellulose and cellulose derivatives, for example, cellulose acetate, triacetate and propionate esters, polypeptides such as collagen, silicone rubber polymers (for example, Dow Silastic), fluorocarbons (for example, Du Pont Teflon), and the like synthetic resins. Examples of suitable fibers made from these materials and methods of their production are disclosed in U.S. Pat. Nos., 3,228,876; 3,583,907; 3,691,068; and 3,821,087.

The fibers can be disposed in a parallel manner as shown in FIG. 2 or can be arranged, for example, in an ordered or randomly distributed mesh form. The fiber bed also can comprise several thicknesses of individual fibers superimposed one upon the other, and generally use of from about one to about 50 such thicknesses of fibers is suitable. Separate layers of fibers can be interspersed with support plates or spacers, if desired. These support plates or spacers can be similar to distributor plate 35 or can be screens and the like means which allow passage of the culture media. The fiber bed also can be a continuous length of fiber which is folded or pleated in a suitable manner to form a plurality of elongate strands or segments which ply the horizontal dimensions of the chamber. A continuous filament also can be wrapped around a screen or support plate and thereby conveniently provide two or more thicknesses of fibers in the bed. If desired, the fiber bed also can be arranged in upright, inclined, folded, sinusoidal, convoluted, or other such configurations as long as a relatively shallow layer of fibers and a relatively short path of media flow are maintained in which the media flow path is directed substantially uniformly through the fiber bed and substantially transverse to the plane of the elongate axes of the fibers.

The fiber bed preferably has a generally square horizontal cross section to facilitate uniform distribution of culture media in all directions.

In an illustrative example of a bed of fibers for a square reactor having bed dimensions of 10 cm × 10 cm., about 300 fibers each having a diameter of 3.4 × $10^{-2}$ cm. ideally can be placed side-by-side in one layer. A reactor with five such fiber layers will then have an effective fiber surface for cell attachment of about 1600 cm.$^2$.

It will be appreciated that the cell reactor of this invention is not limited to the foregoing specific dimensions as other configurations will be apparent from the disclosure herein.

In operation of an illustrative reactor, cell culture medium is fed into chamber 23 through inlet ports 26 and 27. The medium is inoculated through port 29 with a seed culture of a suitable mammalian cell line and the culture incubated at a temperature of from about 20° C to about 40° C, preferably at about 35°–37° C. During the incubation, periodic changes of media can be made, with the spent medium being expelled through outlet port 28 and fresh medium again being supplied through inlet ports 26 and 27. If desired, the culture medium can be aerated by conventional means prior to its being fed into the cell culture reactor. Following incubation, the desired metabolites or by-products of the cell growth can be isolated from the spent medium. Samples of macromolecular materials can be withdrawn through access port 29 at any desired time during the incubation. The reactor preferably is operated continuously whereby inlet ports 26 and 27 and outlet port 28 are kept in an open position and adjusted to any desired rate of flow of culture medium by suitable pumping or gravity feeding means.

The culture medium flows into the lower part of chamber 23 beneath perforated plate 35 which thereby serves as a manifold means to provide uniform distribution of the medium and a flow path which is upward and transverse to the plane of the elongate axes of the fibers. The reduction of the depth of the upper part of chamber 23 in a manner dependent upon its distance from the media outlet 28 assists in the uniform collection of the spent media across the top of the bed of fibers in a manner which corresponds to the demand for the media passing across the fibers, thereby resulting in improved uniformity of flow throughout the chamber.

The combination of the flow path which is transverse to the bed of fibers and the relatively short length of flow through the fiber bed provides a more uniform culture media flow than obtained otherwise with parallel flow through a bundle of capillaries as employed in the prior art. It also promotes a more even distribution of cell growth on the fibers and greater utilization of the available fiber surface. The configuration of the reactor of this invention thereby overcomes the deficiencies in the prior art parallel flow reactors in which cells cannot adequately penetrate the fiber bundle and in which nutrients are utilized at the inlet end with gradual nutrient depletion and undesirable metabolite production as the media flow reaches the distal end of the reactor.

Figure 4:
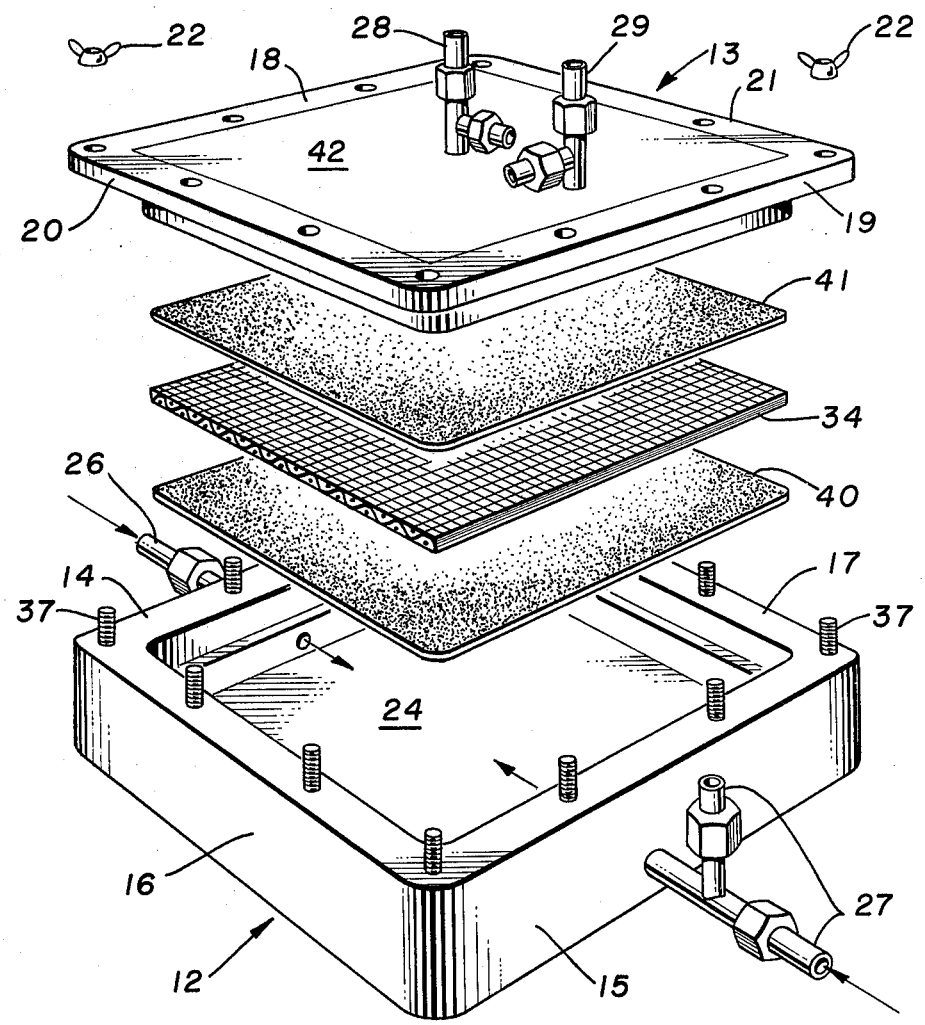
FIG. 4 is an exploded view of another embodiment of the invention.

Referring now to FIG. 4, a modified cell culture reactor of this invention comprising lower and upper housing parts 12 and 13, respectively, is disclosed. Media inlets 26 and 27, and media outlet 28 are essentially the same as in FIGS. 1 to 3, as is access port 29 and the layer of fibers 34. However, a micrometallic filter 40 has been substituted for the perforated distributor plate 35 of FIGS. 1 to 3. The micrometallic filter can be made of stainless steel, for example, and preferably has a pore size ranging from about 0.5 to about 10 microns. It advantageously provides a still more even distribution of culture media than provided by distributor plate 35. The fiber bed also can be sandwiched between a pair of micrometallic filters, in which case the lower filter 40 serves as a distributor plate while the upper filter 41 serves as a diffusion barrier to prevent cells from passing through the outlet port and to stop back-flow of spent media. The upper filter preferably has a pore size ranging from about 10 to about 100 microns. In the latter embodiment, the access port 29 should be located below the horizontal plane of the upper filter, and the top 42 of the reactor preferably will be flat rather than concave as shown in FIGS. 1–3.

Figure 5:
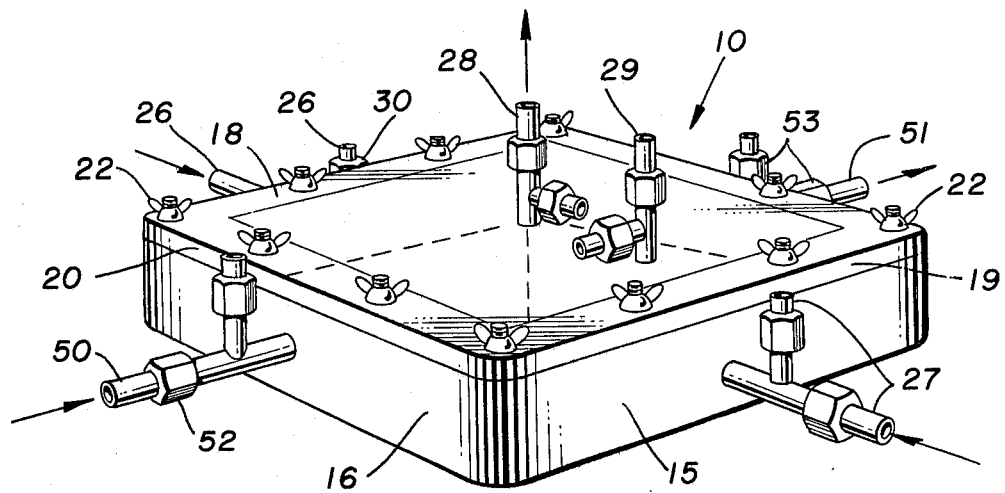
FIG. 5 is a perspective of yet another embodiment of the invention.

Referring to FIG. 5, a cell culture reactor 10 similar to that of FIGS. 1 to 3 is disclosed except that additional means are provided for aeration during the incubation. In this embodiment, the elongate fiber segments are hollow and permeable to air and oxygen, and the reactor is provided with gas inlet and outlet conduit means for communicating with the interior of the hollow fibers. Thus, oppositely disposed gas inlet port 50 and gas outlet port 51 are provided in the housing endwalls 16 and 17, respectively. Gas inlet port 50 permits the entry of air or oxygen through a header in endwall 16 and thence into the open ends of the hollow fibers embedded therein, and gas outlet port 51 permits the removal of exhaust gas from the other ends of the fibers similarly embedded in a header in endwall 17. Fresh culture media enters inlet ports 26 and 27 and spent media is expelled through outlet port 28 as before. Similarly, access for inoculation and sampling is obtained through port 29 as in the embodiment of FIGS. 1 to 3. Adapters 52 and 53 facilitate control of the flow of air or oxygen through the cell culture reactor.

It will be appreciated that many other modifications and variations can be made to the particular embodiments of the invention described hereinbefore without departing from the basic and novel concepts of the invention. For example, other ports such as overflow ports or additional access and feed ports can be provided in the reactor at various convenient locations in the reactor walls. In the embodiments having a plurality of fiber layers, suitable spacers can be employed to impart any desired spaced-apart relationship between the respective layers. The separable upper and lower housing parts can have other suitable shoulder means to provide fluid-tight engagement of the parts. The ends of the fibers can be secured to the sidewalls or endwalls of the reactor or they can be secured in a removable header with potting means such as epoxy and the like settable organic cement materials which can act as a sealant for the fibers. The media inlet ports can additionally have small openings circumferentially spaced about a tubular conduit leading into the reactor chamber to provide a radial dispersion of the fresh culture media.

The shallow bed cell culture reactor of this invention also lends itself to multiple unit configurations. For example, a plurality of the reactors can be readily shelved in an incubator to provide a cell culturing system with all the advantages described herein on a large scale basis.

The materials of construction of the reactor can be metal or plastic materials which lend themselves to fabrication of a relatively rigid structure. Injection molded plastic parts and fabricated metal parts generally can be used for the reactor. Use of clear plastic materials such as, for example, polycarbonate, polystyrene and methyl acrylate plastics, are preferred when it is desired to facilitate visual observation of the cell growth. Use of stainless steel is preferred for its adaptability to steam sterilization. In general, biologically inert materials should be used for fabrication of any parts of the reactor which will come into contact with the culture media and the growth products.

The following examples will further illustrate the invention although it will be appreciated that the invention is not limited to these specific examples. Thus, the particular cell lines and culture media used in these examples have been employed merely as representative of cell lines and culture media well-known in the art and the invention is not limited thereto. For example, other established mammalian cell lines such as human lung fibroblast (WI-38), rhesus monkey kidney cells (MK-2), and cervical carcinoma cells (HeLa), and other conventional culture media such as Eagle's basal medium and Earle's or Hank's balanced salt solutions can be used in the method and apparatus of the invention. So also, the specific inoculation, incubation and harvesting procedures employed in these examples are for illustrative purposes only and the inventors are not bound by these specific procedures. Other well-known cell culture procedures can be adapted to the method and apparatus of this invention as will be apparent to the person skilled in the art.

EXAMPLE 1

Simian virus 40 transformed 3T3 mouse embryo fibroblast (SV3T3) cells were grown to confluency in a 75 cm.$^2$ Falcon tissue culture flask containing 10 ml. of a culture medium consisting of Dulbecco's modified Minimum Essential Medium (MEM) containing 10% fetal calf serum. After removing the spent culture medium from the flask, the cell growth was trypsinized with 2 ml. of 0.25% trypsin in phosphate buffered saline for several minutes and the trypsin was then inactivated by dilution with another 10 ml. portion of the same culture medium. The cells were dispersed and then transferred to a sterile syringe for inoculation of a cell culture reactor as follows.

A flat bed cell culture reactor of the present invention as described hereinbefore was gas sterilized with ethylene oxide, washed with sterile water to remove ethylene oxide residue and then equilibrated by priming with Dulbecco's modified Minimum Esssential Medium (MEM) containing 2% fetal calf serum. The reactor was constructed of Plexiglas methyl acrylate plastic and contained a fiber bed having dimensions of 4 inches by 4 inches by one-half inch deep. The bed consisted of 472 linear feet of a continuous strand of hollow capillary fiber wrapped around three nylon polyester open-mesh screens in substantially uniform thickness. The fiber strand had an outside diameter of 340 microns and was spun from Amicon XM-50 (polyvinyl chloride-acrylic copolymer) plastic. A 4 inch by 4 inch by 1/8 inch thick perforated distributor plate was disposed directly beneath the fiber bed.

The reactor was inoculated with 10 ml. of the above-prepared cell suspension (containing $5 \times 10^6$ cells per ml) and incubated at 37° C for five hours with occasional shaking to promote a more even attachment of cells to the fibers. Following the inoculation, Dulbecco's modified Minimum Essential Medium containing 2% fetal calf serum was pumped into the reactor at the rate of 10 ml. per hour and directed through the perforated distributor plate in an upward flow path transverse to the horizontal plane of the elongate axis of the fibers.

The flow rate was gradually increased to a maximum rate of 60 ml. per hour as the cell density increased, with incubation being terminated after 24 days.

At the termination of incubation, the cells were harvested by dismantling the reactor and thoroughly washing the reactor chamber contents in normal physiological saline. The cells that sloughed off in the wash, and the fiber bed with other cells still attached to the fibers (the majority of the cells), were treated with 1N NaOH for 15 hours to digest the entire cell growth. The digest was then frozen and retained for DNA analysis to estimate the number of cells harvested.

The above cell culturing procedure was repeated in a similar flat bed reactor except that the total incubation time was 59 days.

For comparative purposes, the foregoing cell culture procedures were repeated in a cartridge type cell culture reactor employing parallel fluid flow and a fiber surface equivalent to that of the flat bed reactor. About 800 individual hollow capillary fibers of the same material and diameter as above were arranged in a cartridge bundle 2 cm. in diameter and 20 cm. in length. The culture medium, instead of being directed transverse to the bed of fibers as with the flat bed reactor, flowed from the inlet at one end of the cartridge to the outlet at the other end of the cartridge. Separate incubations were carried out for 24 hours and 59 hours as above the flat bed cell culture reactor.

The DNA analyses for the cells harvested in the above tests are set forth in the following table:

| Reactor Type | Incubation Time in Days | Cell Analysis mg. DNA | Cell Equivalent* |
|---|---|---|---|
| Flat Bed | 24 | 18.374 | $1.837 \times 10^9$ |
| Flat Bed | 59 | 18.84 | $1.84 \times 10^9$ |
| Cartridge | 24 | 4.668 | $0.4668 \times 10^9$ |
| Cartridge | 59 | 11.836 | $1.18 \times 10^9$ |

*Estimated at 10 μg. DNA = $10^6$ cells

In addition to producing a greater number of cells more rapidly as shown above, the flat bed reactor provided a more uniform attachment of cells over the available fiber surface than did the cartridge reactor.

EXAMPLE 2

The cell culture procedures of Example 1 were repeated in a flat bed reactor of this invention using a fiber bed comprising:

(a) polysulfone fiber having an outside diameter of 560 microns and a total length of 414 feet, and
(b) polyacrylonitrile fiber having an outside diameter of 757 microns and a total length of 293 feet.

The cell harvests were estimated by DNA analysis to be equivalent too:
(a) $1.9 \times 10^9$ cells from the polysulfone fibers after 31 days of incubation, and
(b) $2.295 \times 10^9$ cells from the polyacrylonitrile fibers after 34 days of incubation.

EXAMPLE 3

Baby hamster kidney (BHK) cells (ATCC No. CCL 10) are cultured in a sterilized flat bed cell culture reactor of this invention, using Dulbecco's modified Minimal Essential Medium containing 10% fetal calf sersum, and aeration of the medium over a 23 day incubation period. Similar good cell propagation results as in Examples 1 and 2 obtained.

In the foregoing examples, the Dulbecco's modified Minimum Essential Medium is a standard commercially available culture medium obtained from Microbiological Associates, Bethesda, Maryland, under Catalog Number 11–305, as Dulbecco's MEM, 4.5 grams per liter glucose; see In Vitro, Vol. 6. No. 2, pp. 89–94 (1970).

Various other modifications and adaptations of the invention will be apparent to the person skilled in the art after reading the foregoing disclosure without departing from the spirit and scope of the invention and it is intended that all such modifications and adaptations come within the scope of the appended claims.

What is claimed is:

1. In the method of culturing mammalian cells in vitro whereby the cell growth attaches onto a plurality of elongate fibers disposed in a cell culture reactor having culture medium inlet and outlet means, the improvement comprising employing said fibers in a shallow layer configuration and distributing the culture medium with distributor plate means in a flow path substantially uniformly through said fiber layer and substantially, transverse to the plane of the elongate axes of said fibers.

2. The method of claim 1 in which the distributing is carried out by causing the culture medium to flow through an inlet distributor plate having a plurality of small openings therethrough and being positioned substantially parallel to said fiber layer and between said fiber layer and said medium inlet means.

3. The method of claim 1 in which the distributor plate is a micrometallic filter.

4. The method of claim 3 in which the micrometallic filter has a pore size of from about 0.5 to about 10 microns.

5. The method of claim 3 in which an outlet micrometallic filter having a pore size of from about 10 to about 100 microns is positioned substantially parallel to said fiber layer and between said fiber layer and said medium outlet means.

6. The method of claim 1 in which the fiber layer comprises from one to about 50 thicknesses of individual fibers.

* * * * *